(12) United States Patent
Harada et al.

(10) Patent No.: US 8,264,543 B2
(45) Date of Patent: Sep. 11, 2012

(54) RADIATION IMAGE CAPTURING SYSTEM FOR CONTROLLING A PLURALITY OF IMAGE CAPTURING APPARATUSES

(75) Inventors: Daiki Harada, Kanagawa-ken (JP); Naoki Mochizuki, Kanagawa-ken (JP); Yasunori Ohta, Kanagawa-ken (JP); Hiroshi Fukuda, Kanagawa-ken (JP); Kazuharu Ueta, Kanagawa-ken (JP); Eiichi Kito, Kanagawa-ken (JP); Naoyuki Nishino, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 686 days.

(21) Appl. No.: 12/385,151

(22) Filed: Mar. 31, 2009

(65) Prior Publication Data

US 2009/0256915 A1    Oct. 15, 2009

(30) Foreign Application Priority Data

Apr. 2, 2008   (JP) .................................. 2008-096337

(51) Int. Cl.
*H04N 5/30* (2006.01)

(52) U.S. Cl. ............ 348/162; 378/37; 378/62; 250/581; 250/370.08

(58) Field of Classification Search .................. 348/162; 378/37, 62–63, 101; 250/580–582, 370.08–370.1
See application file for complete search history.

(56) References Cited

U.S. PATENT DOCUMENTS

| | | | | |
|---|---|---|---|---|
| 5,018,177 | A | * 5/1991 | McDavid et al. | ............... 378/62 |
| 7,715,524 | B2 | * 5/2010 | Yamakita | ......................... 378/37 |
| 8,184,162 | B2 | * 5/2012 | Watanabe | ..................... 348/162 |
| 2002/0080918 | A1 | 6/2002 | Sako | |
| 2008/0240346 | A1 | * 10/2008 | Kashiwagi et al. | ............. 378/37 |
| 2010/0259409 | A1 | * 10/2010 | Kuwabara et al. | ....... 250/370.08 |

FOREIGN PATENT DOCUMENTS

| | | |
|---|---|---|
| EP | 1103219 | 5/2001 |
| EP | 1389769 | 2/2004 |
| EP | 1389869 | 2/2004 |
| JP | 2006-247137 | 9/2006 |

* cited by examiner

*Primary Examiner* — Bharat N Barot
(74) *Attorney, Agent, or Firm* — Jean C. Edwards, Esq.; Edwards Neils PLLC

(57) ABSTRACT

A radiation image capturing system includes at least one image capturing apparatus including a radiation detector, at least one image capturing apparatus including a stimulable phosphor panel for generating radiation image information, which is readable by an image reading apparatus, and at least one control device for controlling at least the image capturing apparatus and the image reading apparatus based on image capturing instruction information supplied from an external source. The control device includes a change setting unit for changing settings of the image capturing instruction information depending on whether the image capturing apparatus and the image reading apparatus are usable or not, and a controller for controlling the image capturing apparatus and the image reading apparatus based on the changed settings of the image capturing instruction information.

7 Claims, 10 Drawing Sheets

RADIATION IMAGE CAPTURING SYSTEM FOR CONTROLLING A PLURALITY OF IMAGE CAPTURING APPARATUSES

CROSS-REFERENCE TO RELATED APPLICATION

This application claims priority under 35 USC 119 from Japanese Patent Application 2008-096337, filed Apr. 2, 2008, the disclosure of which is incorporated herein by reference.

BACKGROUND OF THE INVENTION

1. Field of the Invention

The present invention relates to a radiation image capturing system for controlling a plurality of image capturing apparatus of different specifications with a processor that is selected according to image capturing instruction information to capture radiation images.

2. Description of the Related Art

In the medical field, there have widely been used radiation image capturing apparatus which apply a radiation to a subject and guide the radiation that has passed through the subject to a radiation detector, which captures a radiation image from the radiation.

One known radiation detector is a stimulable phosphor panel which stores a radiation energy representative of a radiation image in a phosphor. When the stimulable phosphor panel is irradiated with stimulating light, the phosphor emits stimulated light representative of the stored radiation image. The stimulable phosphor panel with the radiation image recorded therein is supplied to an image reading apparatus which reads the stored radiation image as a visible radiation image.

In sites of medical practice such as operating rooms or the like, it is necessary to read recorded radiation image information immediately from a radiation detector for the purpose of quickly and appropriately treating the patient. As a radiation detector which meets such a requirement, there has been developed a radiation detector having a solid-state image capturing device for converting a radiation directly into an electric signal or converting a radiation into visible light with a scintillator and then converting the visible light into an electric signal to read a detected radiation image.

There are available in the art various image capturing apparatus of different specifications for capturing radiation images using radiation detectors depending on the conditions of patients as subjects to be imaged and image capturing conditions including body regions to be imaged. Those different image capturing apparatus are controlled by respective processors of specifications corresponding to the specifications of the image capturing apparatus. According to a known radiographic system, various image capturing apparatus and processors are connected to a radiology information system (RIS) by an in-house network, and image capturing instruction information representative of image capturing conditions set by the RIS which include patient information, image capturing methods, body regions to be imaged, radiation dose, etc. is supplied to the processors, which then control the corresponding image capturing apparatus to capture radiation images (see Japanese Laid-Open Patent Publication No. 2006-247137).

If a process indicated by order information which is supplied from the RIS by a doctor who is taking care of a patient to be imaged cannot be carried out, then a radiological technician (operator) should preferably change the order information depending on the situation at the site where the patient is to be imaged.

However, although conventional radiation image capturing systems can receive order information from the RIS or a console, they are unable to change the order information that has been received.

Hybrid systems which are capable of processing radiation image information captured by a stimulable phosphor panel and a solid-state image capturing device may be required to change part of the order information supplied from the RIS depending on the situation at the site where the patient is to be imaged. In other words, while the conventional radiation image capturing systems are only required to operate according to the supplied order information, the hybrid systems may be required to decide, at the site, which one of the stimulable phosphor panel and the solid-state image capturing device is to be used.

For example, even if a doctor instructs a radiological technician (operator) to capture a radiation image of a patient with a solid-state image capturing device, there are instances where the condition of the patient does not allow a radiation image of the patient to be imaged with the solid-state image capturing device. Specifically, if the patient to be imaged is using a wheelchair, then the patient can be only imaged using a cassette housing the stimulable phosphor panel therein because it is not possible for the patient in the wheelchair to reach the operable range of an image capturing base incorporating the solid-state image capturing device. In such a case, the radiological technician (operator) should preferably be able to change the order information.

However, if the radiological technician (operator) can change the order information, then some problems tend to arise as described below.

According to the conventional radiation image capturing systems, an image capturing apparatus and a processor for controlling the image capturing apparatus are combined in a pair, and radiation image information captured by the image capturing apparatus is corrected by the processor. If image capturing apparatus and processors for controlling the image capturing apparatus are combined in a plurality of pairs, and cassettes incorporating stimulable phosphor panels are used frequently because of the ease with which they are used, then increased radiation image information is supplied to the processors which control the cassettes. Therefore, a queuing time for the process of correcting the radiation image information is long, and it takes a long period of time until the doctor receives corrected radiation image information.

SUMMARY OF THE INVENTION

It is an object of the present invention to provide a radiation image capturing system which makes it possible to share image capturing instruction information for thereby allowing a radiological technician (operator) to easily change order information supplied from an RIS by the doctor who is taking care of a patient to be imaged, depending on the situation at the site where the patient is to be imaged, in case the process according to the order information supplied from the RIS by the doctor is inappropriate to be performed.

Another object of the present invention is to provide a radiation image capturing system which makes it possible to share a process of processing (e.g., correcting) radiation image information for thereby allowing a process of correcting radiation image information captured by an image capturing apparatus to be carried out by not only a processor associated with the image capturing apparatus, but also other processors, so that a queuing time for the process of correcting the radiation image information can greatly be shortened even if image capturing apparatus and processors for controlling the image capturing apparatus are combined in a plurality of pairs.

According to a first aspect of the present invention, there is provided a radiation image capturing system comprising at least one image capturing apparatus including a radiation detector for detecting a radiation which has passed through a subject in a radiation image capturing process, and converting the detected radiation into radiation image information, at least one image capturing apparatus including a stimulable phosphor panel for detecting a radiation which has passed through a subject in a radiation image capturing process, converting the detected radiation into radiation image information, and carrying the radiation image information, the radiation image information being readable by an image reading apparatus, and at least one control device for controlling at least the image capturing apparatus and the image reading apparatus based on image capturing instruction information supplied from an external source, wherein the control device comprises a change setting unit for changing settings of the image capturing instruction information depending on whether the image capturing apparatus and the image reading apparatus are usable or not, and a controller for controlling the image capturing apparatus and the image reading apparatus based on the changed settings of the image capturing instruction information.

According to a second aspect of the present invention, there is also provided a radiation image capturing system comprising at least one image capturing apparatus including a radiation detector for detecting a radiation which has passed through a subject in a radiation image capturing process, and converting the detected radiation into radiation image information, at least one image capturing apparatus including a stimulable phosphor panel for detecting a radiation which has passed through a subject in a radiation image capturing process, converting the detected radiation into radiation image information, and carrying the radiation image information, at least one image reading apparatus for reading and outputting the radiation image information carried by the stimulable phosphor panel or reading, processing, and outputting the radiation image information carried by the stimulable phosphor panel, a plurality of processors associated respectively with the image capturing apparatus, for controlling the associated image capturing apparatus and the image reading apparatus and at least correcting radiation image information acquired by the image capturing apparatus and the image reading apparatus, and at least one control device for controlling at least the processors based on image capturing instruction information supplied from an external source, wherein the control device comprises a correction controller for controlling another processor or another image reading apparatus to correct the radiation image information if the radiation image information acquired by the image capturing apparatus cannot be corrected by an associated one of the processors and the image reading apparatus.

The radiation image capturing system according to the present invention makes it possible to share the image capturing instruction information for thereby allowing a radiological technician (operator) to easily change order information supplied from an RIS by the doctor who is taking care of a patient to be imaged, depending on the situation at the site where the patient is to be imaged, in case the process according to the order information supplied from the RIS by the doctor is inappropriate to be performed.

The radiation image capturing system also makes it possible to share a process of processing (e.g., correcting) radiation image information for thereby allowing a process of correcting radiation image information captured by an image capturing apparatus to be carried out by not only a processor associated with the image capturing apparatus, but also other processors. Therefore, a queuing time for the process of correcting the radiation image information can greatly be shortened even if image capturing apparatus and processors for controlling the image capturing apparatus are combined in a plurality of pairs.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Radiation image capturing system according to preferred embodiments of the present invention will be described in detail below with reference to FIGS. 1 through 10.

Figure 1:
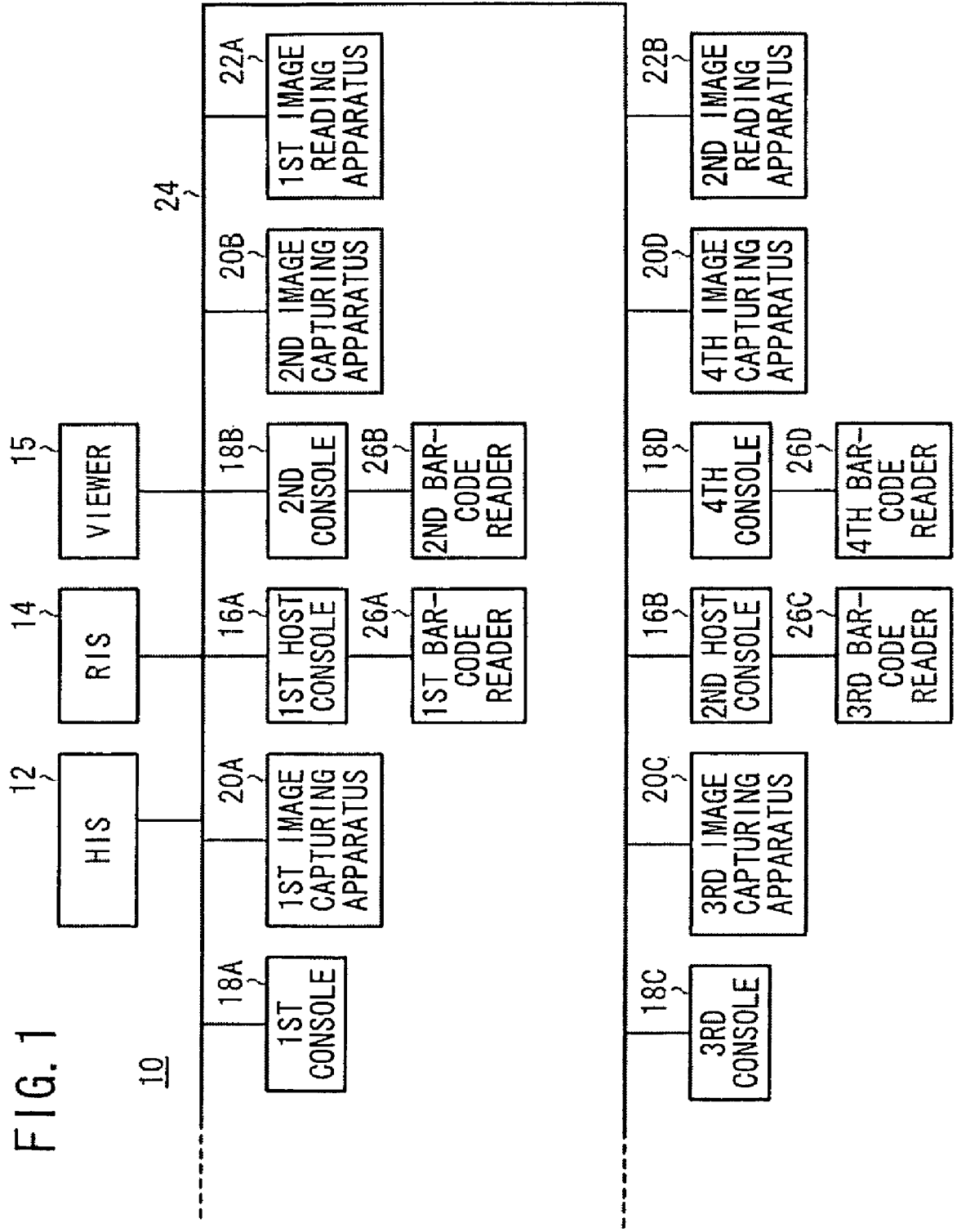
FIG. 1 is a block diagram of a radiation image capturing system according to an embodiment of the present invention.

As shown in FIG. 1, the radiation image capturing system 10 comprises a hospital information system (HIS) 12 for managing medical information processes in a hospital, a radiology information system (RIS) (supplying device) 14 for managing radiation image capturing processes performed in the radiological department of the hospital under the management of the HIS 12, a viewer 15 for displaying radiation images to be interpreted by a doctor for diagnosis, and a first host console 16A (control device) and a second host console 16B (control device) which are placed in a control room near image capturing rooms in the radiological department, for managing various image capturing apparatus of different specifications.

The radiation image capturing system 10 also includes a first console 18A (processor) and a second console 18B (processor) placed in the control room for controlling particular image capturing apparatus, respectively, a first image capturing apparatus 20A for being controlled by the first console 18A, a second image capturing apparatus 20B for being controlled by the second console 18B, and a first reading apparatus (image reading apparatus) 22A for being controlled by the second console 18B and for reading radiation image information captured by the second image capturing apparatus 20B. The first console 18A and the second console 18B are controlled by the first host console 16A.

The radiation image capturing system 10 also includes a third console 18C (processor) and a fourth console 18D (processor) placed in the control room for controlling particular image capturing apparatus, respectively, a third image capturing apparatus 20C for being controlled by the third console 18C, a fourth image capturing apparatus 20D for being controlled by the fourth console 18D, and a second reading apparatus (image reading apparatus) 22B for being controlled by the fourth console 18D and for reading radiation image information captured by the fourth image capturing apparatus 20D. The third console 18C and the fourth console 18D are controlled by the second host console 16B.

The above components of the radiation image capturing system 10 are interconnected by an in-house network 24 in the hospital. If necessary, other consoles, other image capturing apparatus, and other components may also be connected to the in-house network 24.

The first host console 16A acquires, through the in-house network 24, patient information such as the name, gender, age, etc. of a patient which has been set using the HIS 12, and image capturing instruction information including image capturing conditions such as a method of capturing a radiation image, a body region to be imaged, and an image capturing apparatus to be used to capture a radiation image, and, if necessary, a tube voltage, a tube current, and an irradiation time of a radiation, etc. to be set in the radiation source of an image capturing apparatus to be used, the image capturing instruction information being set by the doctor or radiological technician using the RIS 14, and supplies the acquired information to the first console 18A or the second console 18B.

Similarly, the second host console 16B acquires, through the in-house network 24, patient information such as the name, gender, age, etc. of a patient which has been set using the HIS 12, and image capturing instruction information including image capturing conditions such as a method of capturing a radiation image, a body region to be imaged, and an image capturing apparatus to be used to capture a radiation image, and, if necessary, a tube voltage, a tube current, and an irradiation time of a radiation, etc. to be set in the radiation source of an image capturing apparatus to be used, the image capturing instruction information being set by the doctor or radiological technician using the RIS 14, and supplies the acquired information to the third console 18C or the fourth console 18D.

Figure 2:
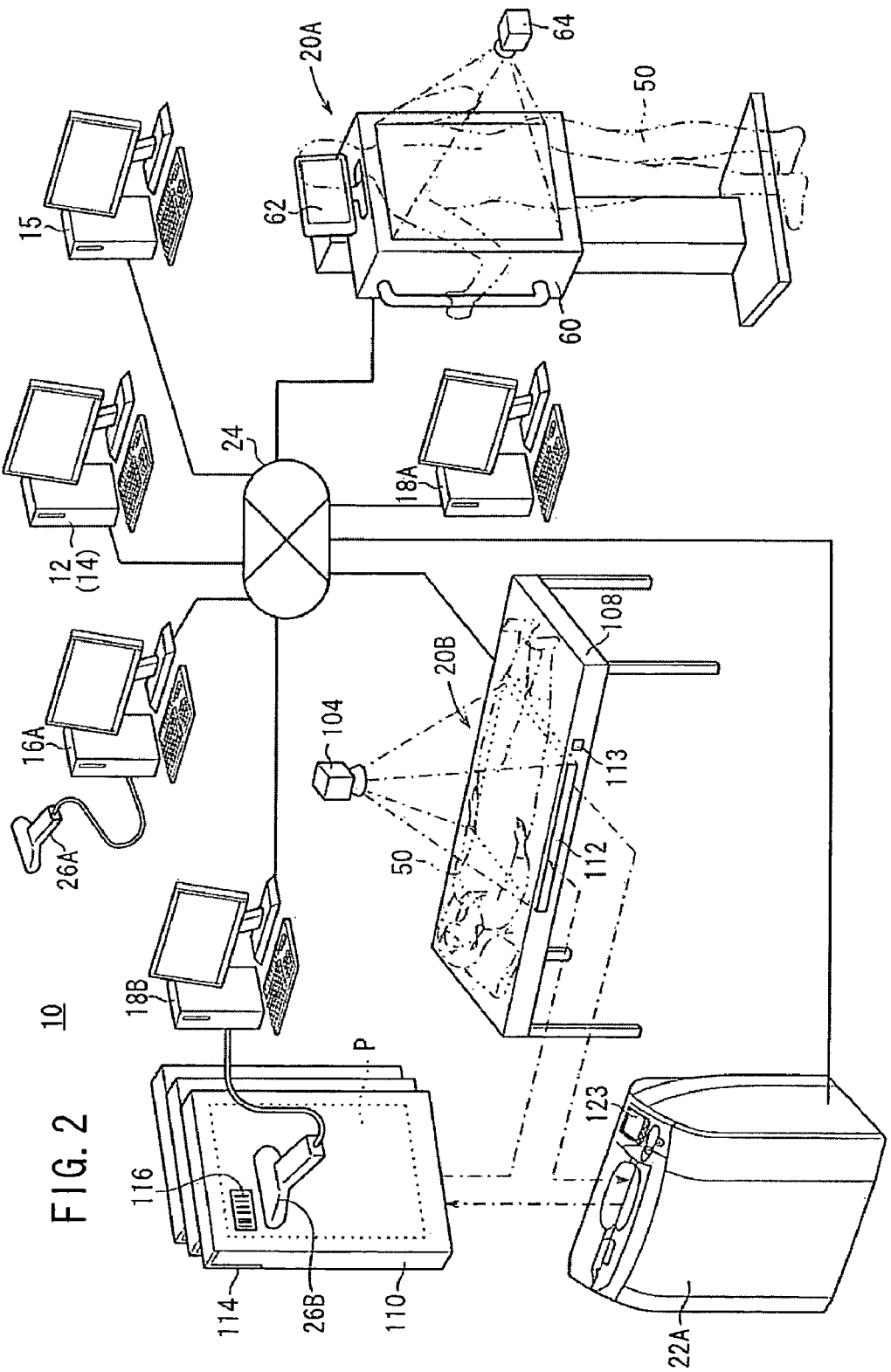
FIG. 2 is a schematic perspective view of the radiation image capturing system to the embodiment of the present invention.

The first host console 16A may perform the processing sequence of the first console 18A or the second console 18B in lieu thereof, and similarly the second host console 16B may perform the processing sequence of the third console 18C or the fourth console 18D in lieu thereof. Therefore, if the first console 18A or the second console 18B is replaced with the first host console 16A, and/or the third console 18C or the fourth console 18D is replaced with the second host console 16B, the radiation image capturing system 10 becomes less costly. To the first host console 16A and the second console 18B, there are connected, respectively, a first bar-code reader 26A and a second bar-code reader 26B for acquiring ID information for identifying a stimulable phosphor panel to be used in the second image capturing apparatus 20B. Similarly, to the second host console 16B and the fourth console 18D, there are connected, respectively, a third bar-code reader 26C and a fourth bar-code reader 26D for acquiring ID information for identifying a stimulable phosphor panel to be used in the fourth image capturing apparatus 20D. In FIG. 2, the second host console 16B, the third console 18C, the fourth console 18D, the third image capturing apparatus 20C, the fourth image capturing apparatus 20D, the second reading apparatus 22B, the third bar-code reader 26C, and the fourth bar-code reader 26D are omitted from the drawing for the sake of brevity.

The first image capturing apparatus 20A, the second image capturing apparatus 20B, and the first reading apparatus 22A will be described as representative apparatus in detail below with reference to FIGS. 2 through 5.

The first image capturing apparatus 20A is an upstanding image capturing apparatus for capturing a radiation image of the chest or the like of a subject 50. The first image capturing apparatus 20A comprises a radiation source 64 for being controlled by a radiation source controller 66 (see FIG. 3), an image capturing base 60 accommodating therein a radiation detector 70 which comprises a solid-state image capturing device to be described later and disposed in confronting relation to the radiation source 64, and a display unit 62 for displaying information required for an image capturing process. The radiation source controller 66 controls the radiation source 64 according to image capturing conditions set by the first host console 16A.

Figure 4:
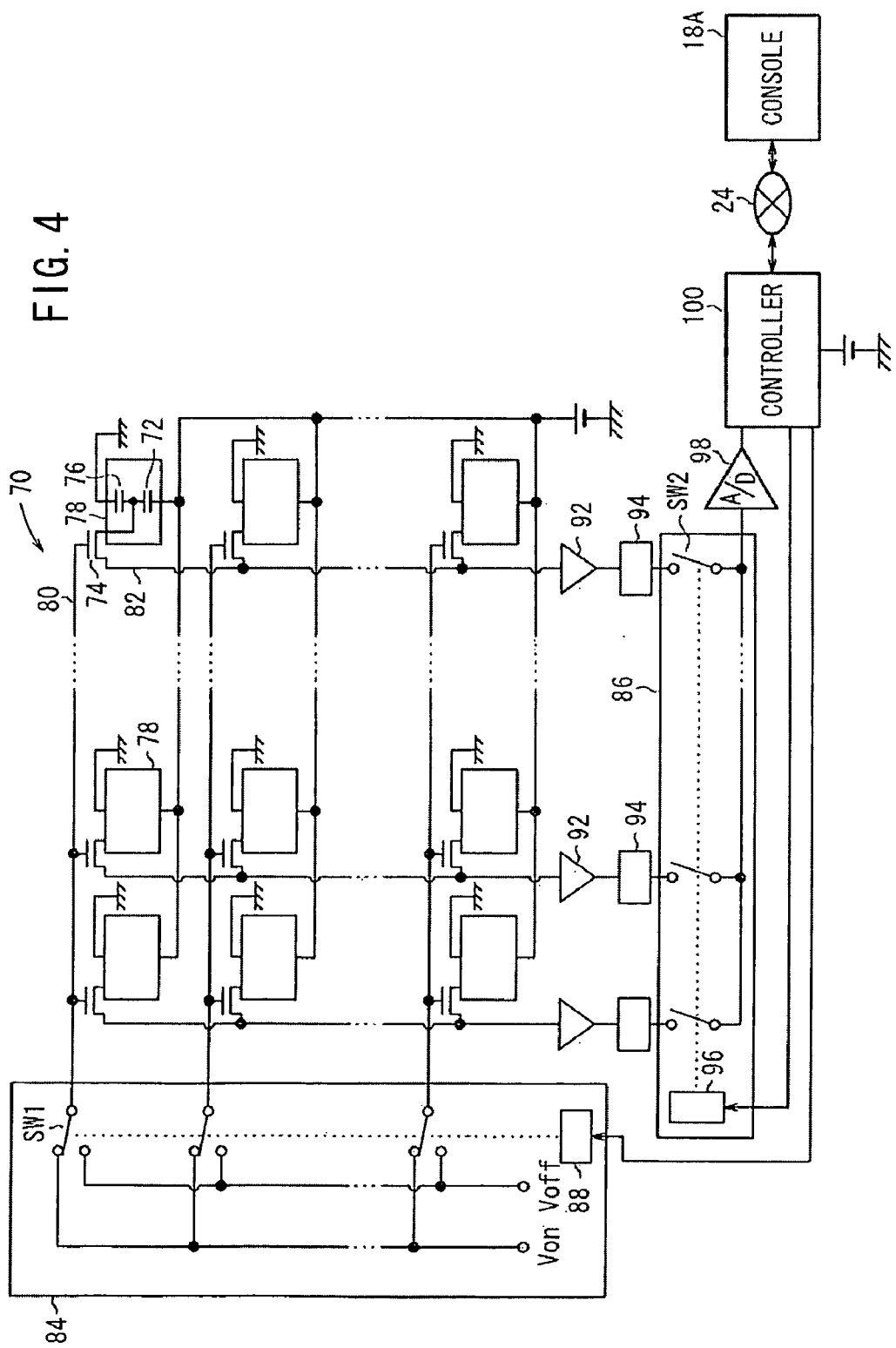
FIG. 4 is a block diagram of a circuit arrangement of a radiation detector used in the radiation image capturing system.

FIG. 4 shows in block form a circuit arrangement of the radiation detector 70 accommodated in the image capturing base 60.

As shown in FIG. 4, the radiation detector 70 comprises an array of thin-film transistors (TFTs) 74 arranged in rows and columns, a photoelectric conversion layer 72 made of a material such as amorphous selenium (a-Se) for generating electric charges upon detection of a radiation, the photoelectric conversion layer 72 being disposed over the array of TFTs 74, and an array of storage capacitors 76 connected to the photoelectric conversion layer 72. When the radiation is applied to the radiation detector 70, the photoelectric conversion layer 72 generates electric charges, and the storage capacitors 76 store the generated electric charges. Then, the TFTs 74 are turned on along each row at a time to read the electric charges from the storage capacitors 76 as an image signal. In FIG. 4, the photoelectric conversion layer 72 and one of the storage capacitors 76 are shown as a pixel 78, and the pixel 78 is connected to one of the TFTs 74. Details of the other pixels 78 are omitted from illustration. Since amorphous selenium tends to change its structure and lose its function at high temperatures, it needs to be used within a certain temperature range. Therefore, some means for cooling the radiation detector 70 should preferably be provided in the image capturing base 60.

The TFTs 74 connected to the respective pixels 78 are connected to respective gate lines 80 extending parallel to the rows and respective signal lines 82 extending parallel to the columns. The gate lines 80 are connected to a line scanning driver 84, and the signal lines 82 are connected to a multiplexer 86 serving as a reading circuit.

The gate lines 80 are supplied with control signals Von, Voff for turning on and off the TFTs 74 along the rows from the line scanning driver 84. The line scanning driver 84 comprises a plurality of switches SW1 for switching between the gate lines 80 and an address decoder 88 for outputting a selection signal for selecting one of the switches SW1 at a time. The address decoder 88 is supplied with an address signal from a controller 100.

The signal lines 82 are supplied with electric charges stored in the storage capacitors 76 of the pixels 78 through the TFTs 74 arranged in the columns. The electric charges supplied to the signal lines 82 are amplified by amplifiers 92 connected respectively to the signal lines 82. The amplifiers 92 are connected through respective sample and hold circuits 94 to the multiplexer 86. The multiplexer 86 comprises a plurality of switches SW2 for successively switching between the signal lines 82 and an address decoder 96 for outputting a selection signal for selecting one of the switches SW2 at a time. The address decoder 96 is supplied with an address signal from the controller 100. The multiplexer 86 has an output terminal connected to an A/D converter 98. A radiation image signal generated by the multiplexer 86 based on the electric charges from the sample and hold circuits 94 is converted by the A/D converter 98 into a digital image signal representing radiation image information, which is supplied to the controller 100. The controller 100 supplies the acquired radiation image information through the in-house network 24 to the first console 18A which controls the first image capturing apparatus 20A.

The second image capturing apparatus 20B is a recumbent image capturing apparatus for capturing a radiation image of a wide area including the chest of the subject 50. The second image capturing apparatus 20B comprises a radiation source 104 for being controlled by a radiation source controller 102 (see FIG. 3) and an image capturing base 108 disposed in confronting relation to the radiation source 104. The image capturing base 108 has a slot 112, defined in a side wall thereof, through which a cassette 110 housing a stimulable phosphor panel P therein can be loaded into the image capturing base 108. The image capturing base 108 has a display unit 113 disposed on a side wall thereof near the slot 112 for displaying that the second image capturing apparatus 20B is being currently selected. The second image capturing apparatus 20B is controlled by the second console 18B through the in-house network 24. The second image capturing apparatus 20B has different specifications from the first image capturing apparatus 20A. The radiation source controller 102 controls the radiation source 104 according to image capturing conditions set by the first host console 16A.

The stimulable phosphor panel P comprises a support body and a stimulable phosphor layer disposed on the support body. The stimulable phosphor layer stores the energy of a radiation X that is applied thereto. When the stimulable phosphor layer is irradiated with stimulating light, it emits stimulated light depending on the stored energy. When the stimulable phosphor layer is irradiated with erasing light, it discharges any remaining energy stored therein and can be reused.

As shown in FIG. 2, the stimulable phosphor panel P housed in the cassette 110 is removable from the cassette 110 when a lid member 114 on the cassette 110 is opened. A bar code 116 which records therein identification information including a unique number for identifying the stimulable phosphor panel P housed in the cassette 110, the size of the stimulable phosphor panel P, the sensitivity of the stimulable phosphor panel P, etc. is applied to an outer surface of the cassette 110. The bar code 116 can be read by the second bar-code reader 26B connected to the second console 18B or the first bar-code reader 26A connected to the first host console 16A.

Figure 5:
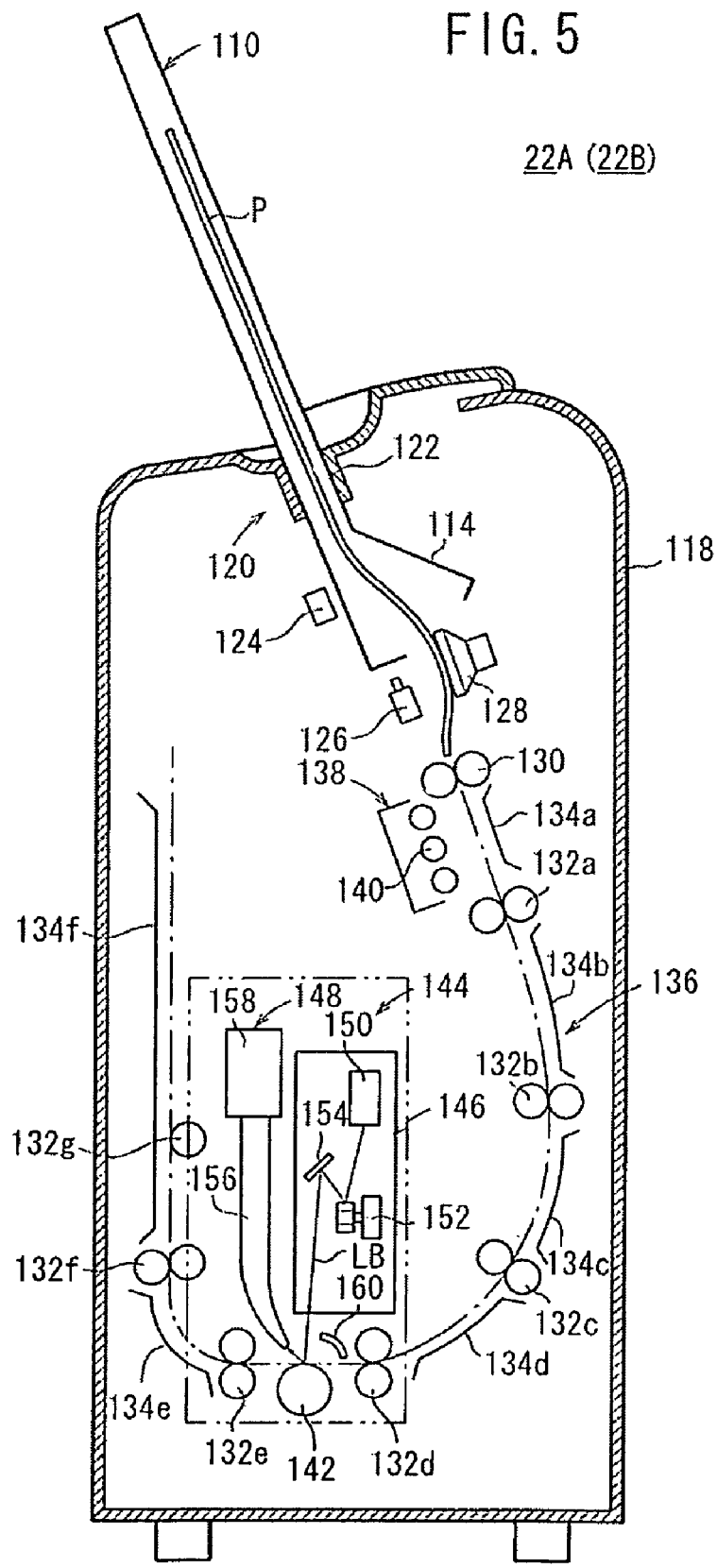
FIG. 5 is a vertical cross-sectional view of a first reading apparatus (second reading apparatus) of the radiation image capturing system.

Radiation image information that has been recorded in the stimulable phosphor panel P is read by the first reading apparatus 22A which is constructed as shown in FIG. 5. The first reading apparatus 22A as well as the second image capturing apparatus 20B is controlled by the second console 18B through the in-house network 24.

As shown in FIG. 5, the first reading apparatus 22A has a cassette loader 120 disposed in an upper portion of a casing 118 and a display unit 123 (see FIG. 2) disposed on the upper portion of the casing 118 for displaying information required for a reading process. The cassette loader 120 has a loading slot 122 for receiving therein the cassette 110 which houses therein the stimulable phosphor panel P with recorded radiation image information. The casing 118 of the reading apparatus 22A accommodates therein, near the loading slot 122, a bar-code reader 124 for reading the identification information recorded in the bar code 116 on the cassette 110, an unlock mechanism 126 for unlocking the lid member 114 of the cassette 110, a suction cup 128 for attracting and removing the stimulable phosphor panel P from the cassette 110 at the time the lid member 114 is opened, and a pair of nip rollers 130 for gripping and feeding the stimulable phosphor panel P removed by the suction cup 128.

The nip rollers 130 are followed by a plurality of feed rollers 132a through 132g and a plurality of guide plates 134a through 134f which jointly make up a curved feed path 136. The curved feed path 136 extends downwardly from the cassette loader 120, then extends substantially horizontally at its lowermost portion, and then extends substantially vertically upwardly. The curved feed path 136 thus shaped is effective to make the first reading apparatus 22A small in size.

Between the nip rollers 130 and the feed rollers 132a, there is disposed an erasing unit 138 for erasing radiation image information remaining in the stimulable phosphor panel P from which desired radiation image information has been read. The erasing unit 138 has a plurality of erasing light sources 140 such as cold cathode tubes or the like for emitting erasing light.

A platen roller 142 is disposed between the feed rollers 132d, 132e which are positioned in the lowermost portion of the curved feed path 136. The platen roller 142 is disposed beneath a scanning unit 144 for reading the desired radiation image information recorded in the stimulable phosphor panel P.

The scanning unit 144 comprises a stimulator 146 for emitting a laser beam LB as stimulating light to scan the stimulable phosphor panel P and an image reader 148 for reading stimulated light emitted from the stimulable phosphor panel P which is stimulated by the laser beam LB, the stimulated light being representative of the radiation image information.

The stimulator 146 comprises a laser oscillator 150 for outputting the laser beam LB, a rotary polygon mirror 152 for deflecting the laser beam LB in a main scanning direction across the stimulable phosphor panel P, and a reflecting mirror 154 for reflecting the laser beam LB to the stimulable phosphor panel P as it passes over the platen roller 142.

The image reader 148 comprises a light guide 156 having a lower end disposed near the stimulable phosphor panel P over the platen roller 142, and a photomultiplier 158 connected to an upper end of the light guide 156 for converting the stimulated light from the stimulable phosphor panel P into an electric signal which represents the radiation image information stored in the stimulable phosphor panel P. A light collecting mirror 160 for increasing the efficiency with which to collect the stimulated light from the stimulable phosphor panel P is disposed near the lower end of the light guide 156. The photomultiplier 158 supplies the electric signal representing the radiation image information, which is processed (e.g., corrected) by an image processor in the first reading apparatus 22A. The radiation image information from the image reader 148 is supplied to the second console 18B through the in-house network 24. The processed radiation image information from the image processor is also supplied to the second console 18B and other consoles through the in-house network 24.

The third image capturing apparatus 20C, the fourth image capturing apparatus 20D, and the second reading apparatus 22B are essentially identical in structure to the first image capturing apparatus 20A, the second image capturing apparatus 20B, and the first reading apparatus 22A, and will not be described in detail below.

Figure 3:
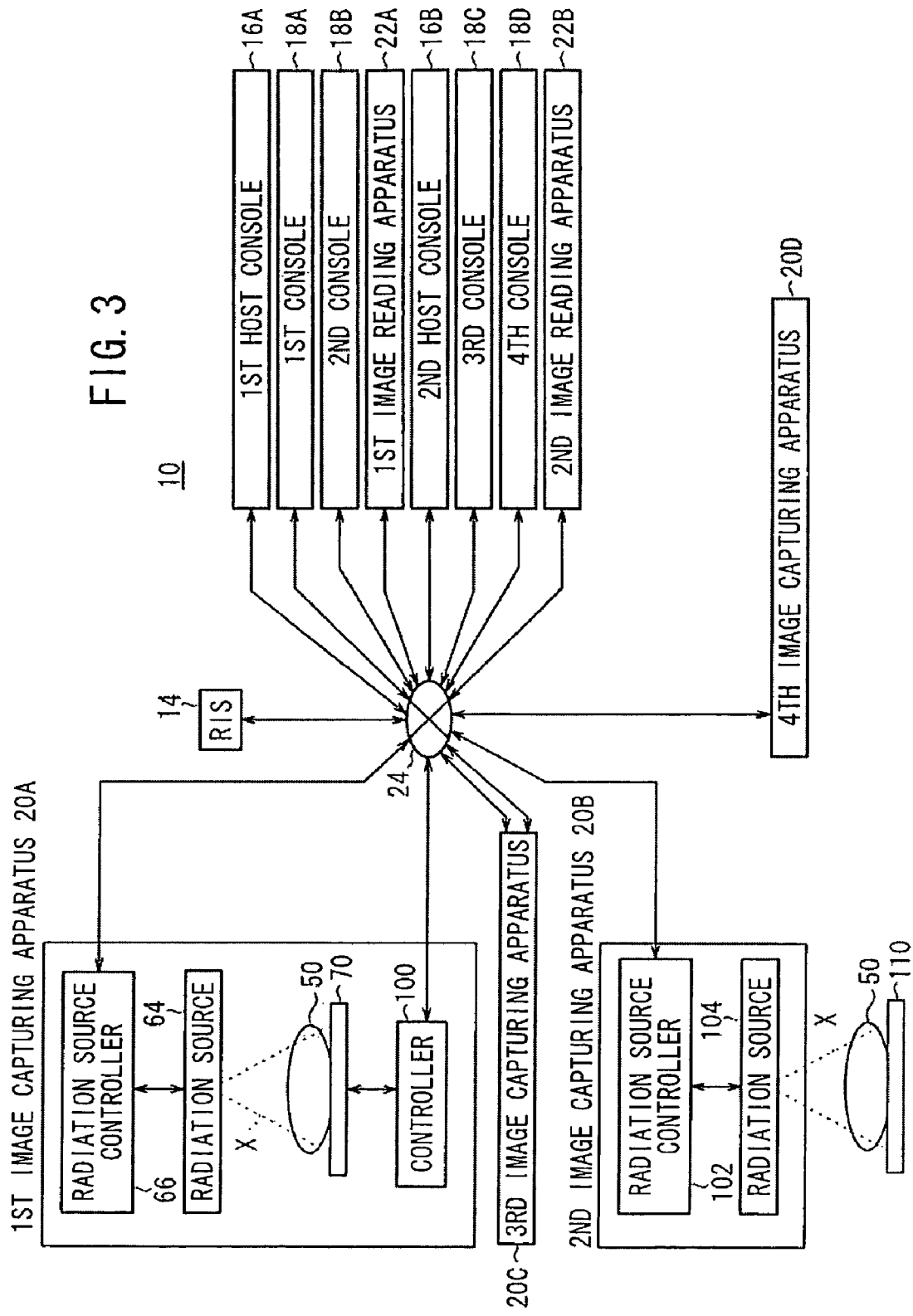
FIG. 3 is a block diagram of the radiation image capturing system, showing configurational details of a first image capturing apparatus and a second image capturing apparatus thereof.

As shown in FIG. 3, a controller 200 (see FIG. 6) of the first host console 16A exchanges necessary information, through the in-house network 24, with the RIS 14, the first console 18A, the second console 18B, the first image capturing apparatus 20A, the second image capturing apparatus 20B, the first reading apparatus 22A, the second host console 16B, the third console 18C, the fourth console 18D, the third image capturing apparatus 20C, the fourth image capturing apparatus 20D, and the second reading apparatus 22B.

Figure 6:
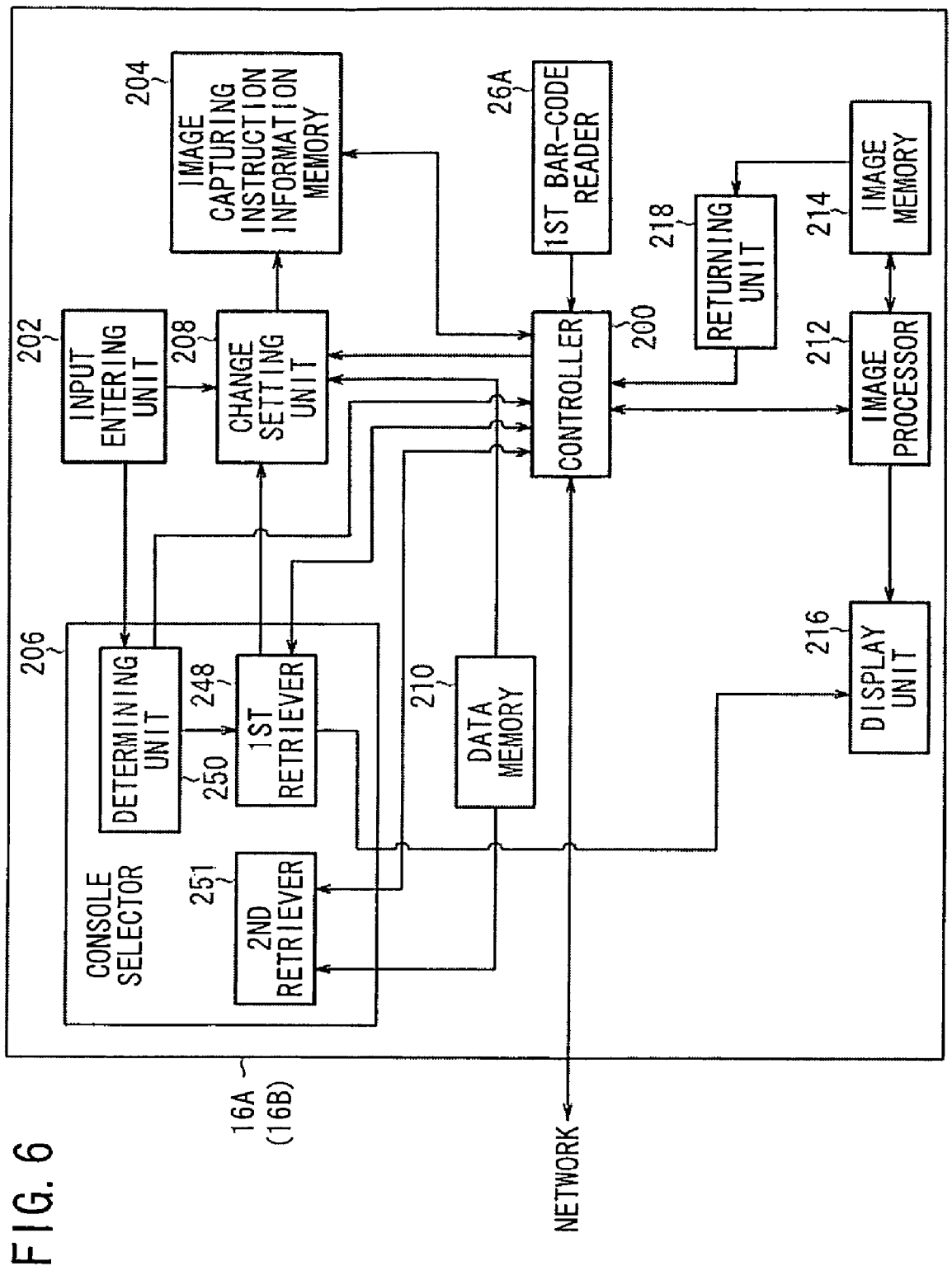
FIG. 6 is a block diagram of a first host console (second host console) of the radiation image capturing system.

As shown in FIG. 6, the first host console 16A comprises an input entering unit 202 operable by the radiological technician, an image capturing instruction information memory 204 for storing image capturing instruction information set by the RIS 14, a change setting unit 208 for changing settings of the image capturing instruction information stored in the image capturing instruction information memory 204 based on input information from the input entering unit 202 or information from a console selector 206 to be described later, and a dada memory 210 for storing various parameters.

The first host console 16A also comprises an image processor 212 for processing (e.g., correcting) radiation image information acquired by the first image capturing apparatus 20A or the first reading apparatus 22A or radiation image information from a console which has issued a correction request, an image memory 214 for storing the processed radiation image information, a display unit 216 for displaying the processed radiation image information etc., and a returning unit 218 for, if a correction request is issued, returning the processed radiation image information to the console which has issued the correction request.

The second host console 16B is essentially identical in configuration to the first host console 16A described above, and will not be described in detail below.

Figure 7:
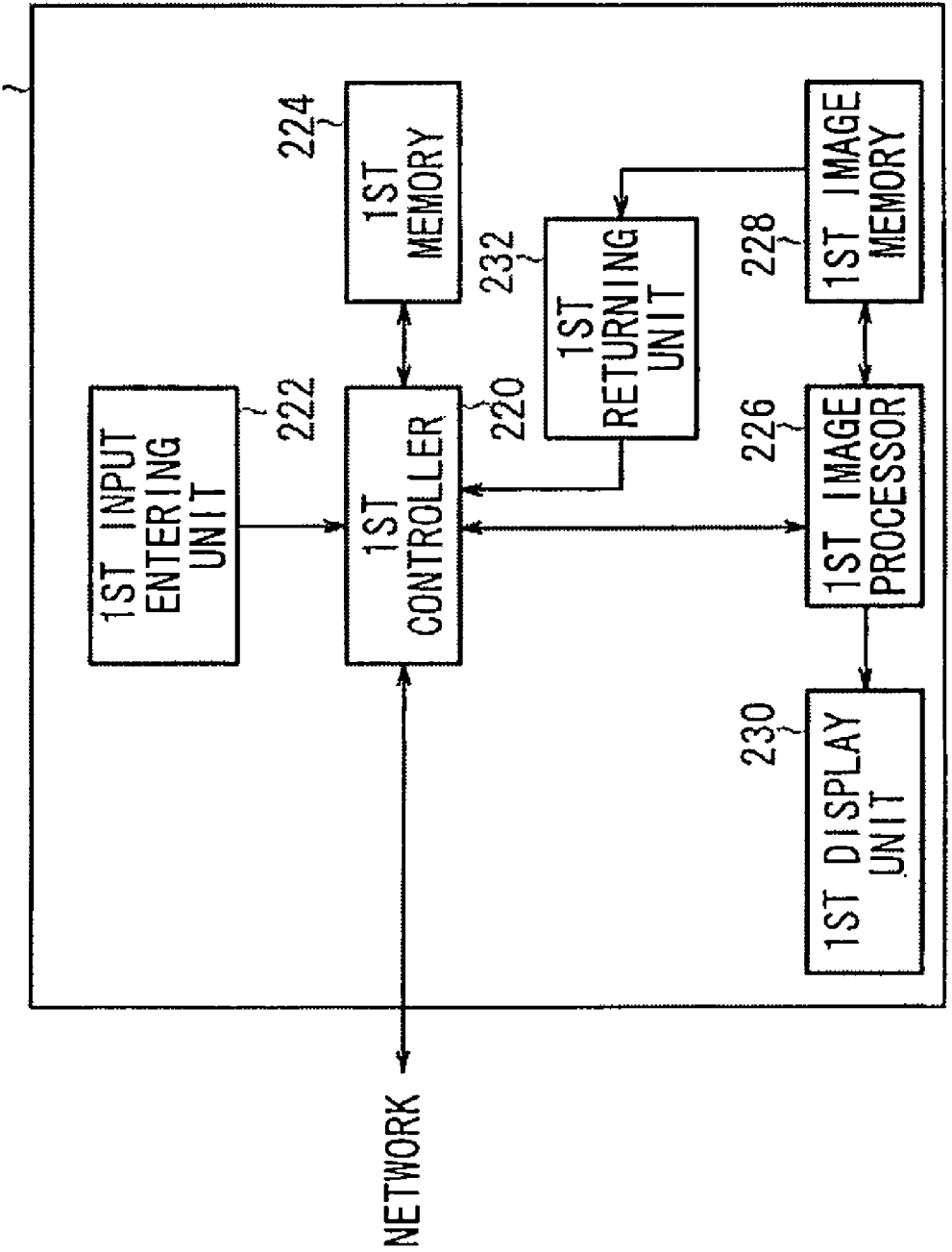
FIG. 7 is a block diagram of a first console (third console) of the radiation image capturing system.

As shown in FIG. 7, the first console 18A comprises a first controller 220 for controlling the transmission and reception of data through the in-house network 24, a first input entering unit 222 operable by the radiological technician, a first memory 224 for storing image capturing instruction information sent through the in-house network 24, a first image processor 226 for processing (e.g., correcting) radiation image information acquired by the first image capturing apparatus 20A or radiation image information from a console which has issued a correction request, a first image memory 228 for storing the processed radiation image information, a first display unit 230 for displaying the processed radiation image information etc., and a first returning unit 232 for, if a correction request is issued, returning the processed radiation image information to the console which has issued the correction request. The third console 18C is also of the configuration shown in FIG. 7.

Figure 8:
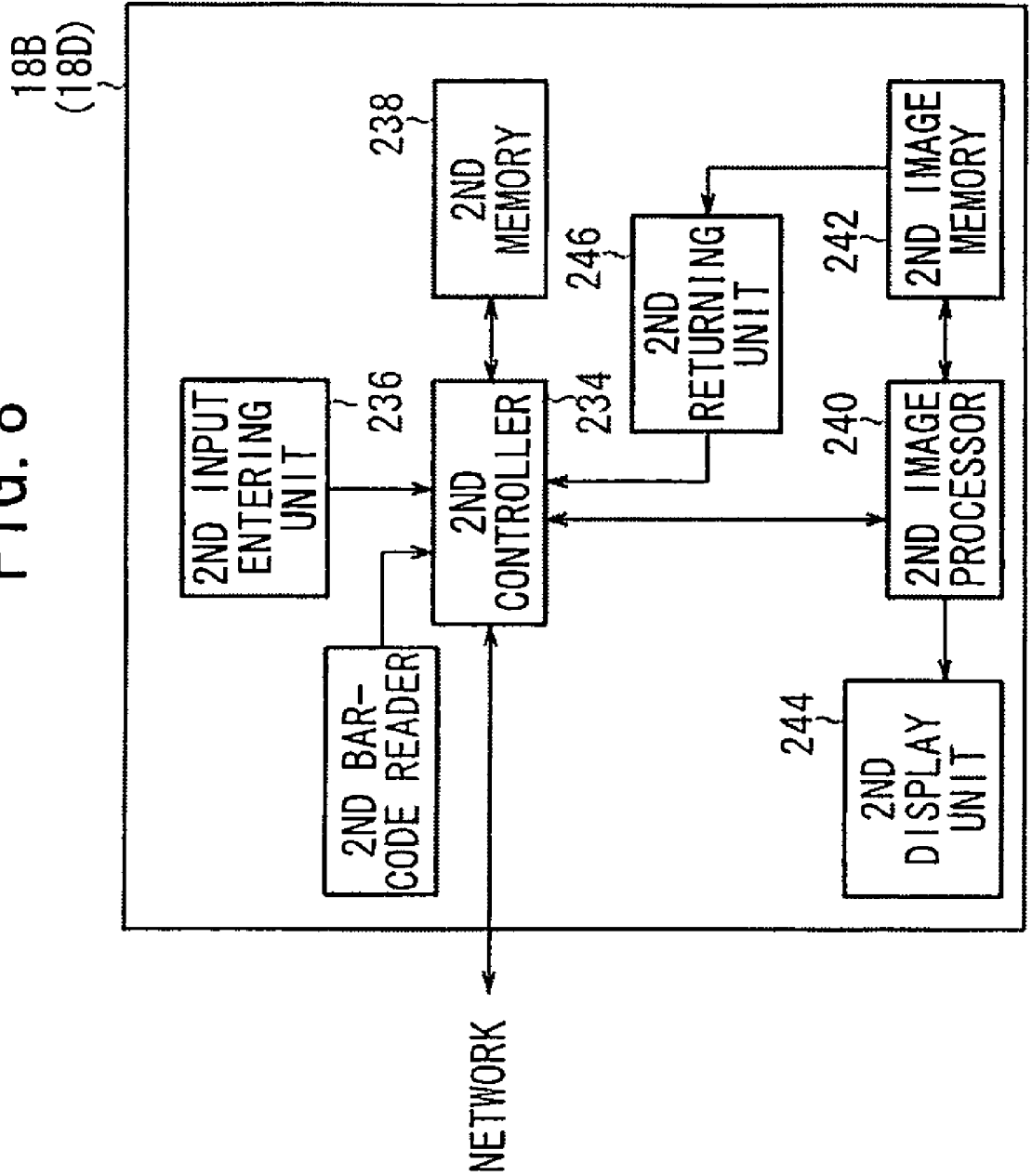
FIG. 8 is a block diagram of a second console (fourth console) of the radiation image capturing system.

As shown in FIG. 8, the second console 18B comprises a second controller 234 for controlling the transmission and reception of data through the in-house network 24, a second input entering unit 236 operable by the radiological technician, a second memory 238 for storing image capturing instruction information sent through the in-house network 24, a second image processor 240 for processing (e.g., correcting) radiation image information acquired by the first reading apparatus 22A or radiation image information from a console which has issued a correction request, a second image memory 242 for storing the processed radiation image information, a second display unit 244 for displaying the processed radiation image information etc., and a second returning unit 246 for, if a correction request is issued, returning the processed radiation image information to the console which has issued the correction request. The fourth console 18D is also of the configuration shown in FIG. 8.

As shown in FIG. 6, the console selector 206 of the first host console 16A comprises a first retriever 248 for retrieving another image capturing apparatus which is usable if the image capturing apparatus specified by the image capturing instruction information stored in the image capturing instruction information memory 204 is not usable, a determining unit 250 for determining whether a retrieving process of a retriever is necessary or not, and a second retriever 251 for retrieving a console which is capable of processing (e.g., correcting) radiation image information.

The above case where the image capturing apparatus specified by the image capturing instruction information is not usable, includes the following situations. For example, the determining unit 250 may determine the image capturing apparatus as being not usable or the radiological technician may perform an input operation through the input entering unit 202 so as to indicate that the image capturing apparatus will not be used.

The determining unit 250 determines whether the processor (the first console 18A or the second console 18B) for controlling the image capturing apparatus (the first image capturing apparatus 20A or the second image capturing apparatus 20B) specified by the image capturing instruction information is capable of performing a next image capturing process or not. Specifically, if the image capturing apparatus specified by the image capturing instruction information is the first image capturing apparatus 20A, then the determining unit 250 instructs the first console 18A to send present status information. The present status information is of a flag configuration which is set or reset by the operating system of the first console 18A in reference to the system status. For example, the present status information is made up of four bits ranging from a 0th bit to a 3rd bit. If the 0th bit is "1", then it indicates that the first console 18A is ready and waiting (it is not busy). If the 1st bit is "1", then it indicates that the first console 18A is controlling the first image capturing apparatus 20A to perform an image capturing process (it is busy) and is unable to perform a next image capturing process immediately. If the 2nd bit is "1", then it indicates that the first console 18A is processing the radiation image information acquired from the first image capturing apparatus 20A or the like and is unable to perform a next image capturing process immediately. If the 3rd bit is "1", then it indicates that the first console 18A or the first image capturing apparatus 20A controlled thereby is suffering a failure. The present status information of the second console 18B, the third console 18C, and the fourth console 18D is the same as the above present status information of the first console 18A.

The determining unit 250 refers to the present status information sent from the first console 18A. If any one of the bits other than the 0th bit thereof is "1", then the determining unit 250 judges that the first console 18A is unable to perform a next image capturing process, and activates the first retriever 248.

The determining unit 250 also refers to input data from the input entering unit 202, and activates the first retriever 248 when the radiological technician enters an input indicating that the specified image capturing apparatus will not be used, through the input entering unit 202.

The first retriever 248 retrieves another console or processor which is capable of controlling an image capturing apparatus to capture radiation image information according to the image capturing instruction information and also of performing its processing sequence. If capturing an image of the chest, an image of the abdomen, or an image of either one of the four limbs, an image capturing apparatus which is able to capture radiation image information according to the image capturing instruction information may be a cassette 110 incorporating the stimulable phosphor panel P therein, a cassette incorporating the radiation detector 70 therein, an upstanding image capturing apparatus, or a recumbent image capturing apparatus. If capturing a mammographic image, an image capturing apparatus which is able to capture radiation image information according to the image capturing instruction information may be an image capturing apparatus dedicated for the capture of an image of a breast.

The first retriever 248 instructs one or more consoles for controlling an image capturing apparatus which is able to capture radiation image information according to the image capturing instruction information, among the second image capturing apparatus 20B, the third image capturing apparatus 20C, and the fourth image capturing apparatus 20D, to send present status information to the first retriever 248. The first retriever 248 then supplies the present status information of one or more consoles where the 0th bit is "1", among the present status information sent to the first retriever 248, to the change setting unit 208, and displays a list of corresponding consoles on the display unit 216.

If the data memory 210 stores a table of console priority levels, then the change setting unit 208 selects the console with the highest console priority level from the retrieved one or more consoles. The information of the selected console is reflected in the image capturing instruction information by the change setting unit 208. The image capturing instruction information with the reflected console information is sent through the controller 200 to the selected console. If the selected console processes the radiation image information from an image reading apparatus, then the image capturing instruction information is also sent to the corresponding reading apparatus.

Alternatively, the radiological technician may select a console. For example, the radiological technician may select one console based on the information of the displayed list of consoles, and enter the information of the selected console through the input entering unit 202. The entered information is reflected in the image capturing instruction information by the change setting unit 208. The image capturing instruction information with the reflected console information is sent through the controller 200 to the selected console. If the selected console processes the radiation image information from an image reading apparatus, then the image capturing instruction information is also sent to the corresponding reading apparatus. If the radiological technician selects a console, then the radiological technician may select a console in a manner to deal with various situations, e.g., may select a console for controlling an image capturing apparatus which is less burdensome for the subject or patient. For example, if the subject 50 uses a wheelchair and an image of the chest of the subject 50 is to be captured, then the first image capturing apparatus 20A shown in FIG. 2 may possibly be unable to position the subject 50 with respect to the image capturing base 60. In this case, if an image capturing apparatus that is capable of capturing an image of the chest of the subject 50 in the wheelchair is connected to the in-house network 24 and a console for controlling such an image capturing apparatus is included in the displayed list, then the radiological technician can select the console.

If a plurality of consoles are retrieved, all the retrieved consoles may be selected to deal with a situation where an image of a body part of the subject 50 is captured by the first image capturing apparatus 20A and an image of another body part of the subject 50 is captured by the second image capturing apparatus 20B. In this case, the change setting unit 208 reflects information entered through the input entering unit 202 by the radiological technician in the image capturing instruction information. The image capturing instruction information with the reflected console information is sent through the controller 200 to the selected consoles. If one or more of the selected console processes the radiation image information from an image reading apparatus, then the image capturing instruction information is also sent to the corresponding reading apparatus.

If the first console 18A, the second console 18B, and the first reading apparatus 22A are unable to correct current radiation image information acquired by the first image capturing apparatus 20A and the first reading apparatus 22A because the first image processor 226, the second image processor 240, and the first reading apparatus 22A are, for example, in the process of correcting previous radiation image information, then the first console 18A, the second console 18B, and the first reading apparatus 22A send a retrieval request to the first host console 16A.

Likewise, if the third console 18C, the fourth console 18D, and the second reading apparatus 22B are unable to correct current radiation image information acquired by the third image capturing apparatus 20C and the second reading apparatus 22B because the first image processor 226, the second image processor 240, and the second reading apparatus 22B, for example, are in the process of correcting previous radiation image information, then the third console 18C, the fourth console 18D, and the second reading apparatus 22B send a retrieval request to the second host console 16B.

For example, when the first host console 16A receives a retrieval request from the first console 18A, the console selector 206 of the first host console 16A activates the second retriever 251. The second retriever 251 instructs other consoles than the first console 18A, which may include the first host console 16A and the second host console 16B, and also the first reading apparatus 22A and the second reading apparatus 22B to send present status information. Then, the second retriever 251 retrieves one or more consoles (and reading apparatus) which have status information whose 2nd bit indicating a status of process is "0" and 3rd bit indicating a status of failure is "0", among the present status information sent from the other consoles, the first reading apparatus 22A, and the second reading apparatus 22B. If there are a plurality of retrieved consoles and reading apparatus, then the second retriever 251 selects consoles and reading apparatus having status information whose 0th bit is "1", i.e., consoles and reading apparatus which are ready and waiting. If there are plurality of consoles and reading apparatus which are ready and waiting, then the second retriever 251 refers to the priority levels of the consoles stored in the data memory 210, and selects one console, e.g., the third console 18C, and one reading apparatus, e.g., the first reading apparatus 22A. The information of the selected console (or reading apparatus) is sent to the first console 18A which has sent the retrieval request. Based on the received information of the selected console, the first controller 220 of the first console 18A sends the radiation image information and the specification information of the first image capturing apparatus 20A to the console, e.g., the third console 18C, or the image reading apparatus, e.g., the first reading apparatus 22A. The selected console (or reading apparatus) receives the radiation image information and the specification information of the first image capturing apparatus 20A from the first console 18A. Thereafter, the image processor processes (corrects) the radiation image information depending on the specifications of the first image capturing apparatus 20A, and then sends the processed radiation image information back to the first console 18A. The first console 18A displays a radiation image based on the radiation image information for the radiological technician to confirm the radiation image, if necessary, and sends the radiation image information to the viewer 15 through the in-house network 24. The doctor then interprets for diagnosis a radiation image that is displayed by the viewer 15 based on the radiation image information.

In the example described above, the correcting process which is normally performed by the first console 18A is performed by the third console 18C (or the first reading apparatus 22A). However, the correcting process may be performed by consoles and reading apparatus in various combinations. For example, the correcting process which is performed by the first console 18A may be performed by the second console 18B, the first host console 16A, the second host console 16B, the fourth console 18D, or the second reading apparatus 22B. The correcting process which is performed by the third console 18C or the fourth console 18D may similarly be performed by other consoles and reading apparatus.

Image capturing apparatus of other specifications, such as a CT (computed tomography) apparatus, an MR (magnetic resonance) apparatus, etc. may also be connected to the in-house network 24, and consoles (processors) for controlling these image capturing apparatus may also be connected to the in-house network 24.

The radiation image capturing system 10 according to the present invention is basically constructed as described above. Operation of the radiation image capturing system 10 will be described below.

First, patient information such as the name, gender, age, etc. of a patient is set using the HIS 12, and image capturing instruction information such as a method of capturing a radiation image, a body region to be imaged, and an image capturing apparatus to be used to capture a radiation image, is set in relation to the patient information using the RIS 14.

The controller 200 of the first host console 16A, for example, that is installed in the radiological department acquires the patient information and the image capturing instruction information from the RIS 14 via the in-house network 24. The radiological technician sets and changes the image capturing instruction information using the input entering unit 202 of the first host console 16A, if necessary. For example, the radiological technician changes the image capturing apparatus which has been set by the doctor using the RIS 14 to an image capturing apparatus which is suitable for the body region to be imaged and the condition of the patient. The change setting unit 208 stores the patient information and the image capturing instruction information that have been acquired or the image capturing instruction information that has been changed or newly set, in the image capturing instruction information memory 204.

Specifically, it is assumed that the doctor selects the first image capturing apparatus 20A using the RIS 14, but the subject 50 is using a wheelchair and cannot be imaged by the first image capturing apparatus 20A. In this case, the radiological technician selects a console, e.g., the second console 18B, for controlling an image capturing apparatus that is less burdensome on the patient (subject) 50, e.g., the cassette 110 housing the stimulable phosphor panel P, from the information of usable consoles displayed on the display unit 216 of the first host console 16A. The radiological technician places the cassette 110 between the wheelchair and the subject 50, and changes the image capturing instruction information about the image capturing apparatus in order to switch to another image capturing process using the radiation source 104 of the second image capturing apparatus 20B.

According to another example, if the second image capturing apparatus 20B which is selected by the doctor cannot be used because it is being in an adjustment process, for example, then the radiological technician changes the image capturing instruction information from an image capturing process using the second image capturing apparatus 20B to an image capturing process using the fourth image capturing apparatus 20D in order to switch to the image capturing process using the fourth image capturing apparatus 20D as an alternative.

Then, the controller 200 of the first host console 16A reads the patient information and the image capturing instruction information from the image capturing instruction information memory 204, and sends the patient information and the image capturing instruction information to the console selected by the console selector 206.

According to still another example, an image of a body region of the subject 50 is captured by the first image capturing apparatus 20A, and an image of another body region of the subject 50 is captured by the second image capturing apparatus 20B. In this case, the console selector 206 selects the corresponding consoles according to the image capturing instruction information for the body regions to be imaged, and sends the patient information and the image capturing instruction information to the consoles.

The consoles which have been supplied with the patient information and the image capturing instruction information perform image capturing processes using the image capturing apparatus controlled thereby according to the image capturing instruction information.

It is assumed that the second console 18B is used to control the second image capturing apparatus 20B to perform an image capturing process on the subject 50. When the second image capturing apparatus 20B is selected, the selection is displayed on the display unit 113 on the side wall of the image capturing base 108 to prompt the radiological technician to guide the subject 50 to the second image capturing apparatus 20B for the image capturing process.

When the second console 18B receives the patient information and the image capturing instruction information from the first host console 16A, the second console 18B sets a tube voltage, a tube current, and an irradiation time of image capturing conditions included in the image capturing instruction information, in the radiation source controller 102 of the second image capturing apparatus 20B.

The radiological technician uses the second bar-code reader 26B connected to the second console 18B to read the bar code attached to the cassette 110, thereby acquiring identification information including a unique number for identifying the stimulable phosphor panel P housed in the cassette 110, the size of the stimulable phosphor panel P, the sensitivity of the stimulable phosphor panel P, etc.

After having loaded the cassette 110 into the slot 112 of the second image capturing apparatus 20B, the radiological technician operates an image capturing switch, not shown, to start an image capturing process. The radiation source controller 102 controls the radiation source 104 according to the set image capturing conditions to apply the radiation X to the subject 50. The radiation X that has passed through the subject 50 is applied to the stimulable phosphor panel P housed in the cassette 110. As a result, radiation image information of the subject 50 is recorded in the stimulable phosphor panel P.

The radiological technician then removes the cassette 110 housing therein the stimulable phosphor panel P with the recorded radiation image information, from the second image capturing apparatus 20B, and thereafter loads the cassette 110 into the cassette loader 120 of the first reading apparatus 22A. The radiological technician can reliably recognize that the reading process is to be carried out by the first reading apparatus 22A, by seeing the display unit 123 on the cassette loader 120 which displays that the first reading apparatus 22A has been selected.

When the cassette 110 is loaded into the cassette loader 120, the bar-code reader 124 in the cassette loader 120 reads the bar code attached to the cassette 110 to acquire the identification information including the unique number, the size, the sensitivity, etc. of the stimulable phosphor panel P. The acquired identification information is compared with the identification information read by the second bar-code reader 26B connected to the second console 18B to confirm the correspondence between the subject 50 and the radiation image information.

After the identification information is read, the unlock mechanism 126 is actuated to unlock and open the lid member 114. The suction cup 128 attracts the stimulable phosphor panel P, removes the stimulable phosphor panel P out of the cassette 110, and feeds the stimulable phosphor panel P between the nip rollers 130. The stimulable phosphor panel P which is gripped by the nip rollers 130 is then fed to a position beneath the scanning unit 144 through the curved feed path 136 made up of the feed rollers 132*a* through 132*g* and the guide plates 134*a* through 134*f*.

Beneath the scanning unit 144, the stimulable phosphor panel P is fed substantially horizontally in an auxiliary scanning direction by the feed rollers 132*d*, 132*e*. At the same time, the laser beam LB output from the laser oscillator 150 of the stimulator 146 is reflected and deflected by the polygon mirror 152 that is rotating at a high speed, and then guided by the reflecting mirror 154 to the stimulable phosphor panel P whose lower surface is supported by the platen roller 142, thereby scanning the stimulable phosphor panel P in a main scanning direction.

By being irradiated with the laser beam LB, the stimulable phosphor panel P is stimulated to emit stimulated light representative of the radiation image information recorded therein. The stimulated light is applied directly or via the light collecting mirror 160 to the lower end of the light guide 156 which is disposed near the stimulable phosphor panel P and extends in the main scanning direction. The stimulated light which has entered the light guide 156 is repeatedly reflected in the light guide 156 and guided to the photomultiplier 158. The photomultiplier 158 converts the stimulated light into an electric signal representative of the radiation image information recorded in the stimulable phosphor panel P. In this manner, the radiation image information recorded in the stimulable phosphor panel P is read by the scanning unit 144 of the image reading apparatus 22A.

The radiation image information thus read by the scanning unit 144 is transmitted to the second console 18B through the in-house network 24. The second console 18B processes the received radiation image information depending on the specifications of the second image capturing apparatus 20B. Then, the second console 18B displays a radiation image based on the processed radiation image information for the radiological technician to confirm the radiation image, and then transmits the radiation image information to the viewer 15 through the in-house network 24. The doctor then interprets for diagnosis a radiation image that is displayed by the viewer 15 based on the radiation image information. If the second console 18B is processing other radiation image information that has already been received thereby, then the console selector 206 of the first host console 16A retrieves another processor capable of performing its processing sequence, and sends the radiation image information acquired from the second image capturing apparatus 20B, to the retrieved other processor, whereby the other processor processes the radiation image information.

It is assumed that the first console 18A is used to control the first image capturing apparatus 20A to perform an image capturing process on the subject 50. When the first image capturing apparatus 20A is selected, the selection is displayed on the display unit 62 on the top of the image capturing base 60 to prompt the radiological technician to guide the subject 50 to the first image capturing apparatus 20A for the image capturing process.

When the first console 18A receives the patient information and the image capturing instruction information from the first host console 16A, the first console 18A sets a tube voltage, a tube current, and an irradiation time of image capturing conditions included in the image capturing instruction information, in the radiation source controller 66 of the first image capturing apparatus 20A.

After having positioned the subject 50 in a given position on the image capturing base 60, the radiological technician operates an image capturing switch, not shown, to start an image capturing process. The radiation source controller 66 controls the radiation source 64 according to the set image capturing conditions to apply the radiation X to the subject 50. The radiation X that has passed through the subject 50 is applied to the radiation detector 70.

The radiation X is converted into electric signals by the photoelectric conversion layer 72 of the pixels 78 of the radiation detector 70 (FIG. 4). The electric signals are stored as electric charges in the storage capacitors 76. The stored electric charges, which represent radiation image information of the patient (subject) 50, are read from the storage capacitors 76 according to address signals which are supplied from the controller 100 to the line scanning driver 84 and the multiplexer 86.

Specifically, in response to the address signal supplied from the controller 100, the address decoder 88 of the line scanning driver 84 outputs a selection signal so as to select one of the switches SW1, which supplies the control signal Von to the gates of the TFTs 74 connected to the gate line 80 corresponding to the selected switch SW1. In response to the address signal supplied from the controller 100, the address decoder 96 of the multiplexer 86 outputs a selection signal, which operates to successively turn on the switches SW2 so as to switch between the signal lines 82, for thereby reading the electric charges stored in the storage capacitors 76 of the pixels 78 connected to the selected gate line 80, through the signal lines 82.

The electric charges (radiation image information) read from the storage capacitors 76 of the pixels 78 connected to the selected gate line 80 are amplified by the respective amplifiers 92, sampled by the sample and hold circuits 94, and supplied to the multiplexer 86. Based on the supplied electric charges, the multiplexer 86 generates and supplies a radiation image signal to the A/D converter 98, which converts the radiation image signal into a digital signal. The digital signal which represents the radiation image information is transmitted from the controller 100 to the first console 18A through the in-house network 24.

Similarly, the address decoder 88 of the line scanning driver 84 successively turns on the switches SW1 to switch between the gate lines 80 according to the address signal supplied from the controller 100. The electric charges stored in the storage capacitors 76 of the pixels 78 connected to the successively selected gate lines 80 are read through the signal lines 82, and processed by the multiplexer 86 and the A/D converter 98 into digital signals, which are transmitted from the controller 100 to the first console 18A through the in-house network 24.

The first console 18A processes the radiation image information represented by the received digital signals depending on the specifications of the first image capturing apparatus 20A. Then, the first console 18A displays a radiation image based on the processed radiation image information for the radiological technician to confirm the radiation image, and then transmits the radiation image information to the viewer 15 through the in-house network 24. The doctor then interprets for diagnosis a radiation image that is displayed by the viewer 15 based on the radiation image information. If the first console 18A is processing other radiation image information that has already been received thereby, then the console selector 206 of the first host console 16A retrieves another processor capable of performing its processing sequence, and sends the radiation image information acquired from the first image capturing apparatus 20A to the retrieved other processor, whereby the other processor processes the radiation image information.

The radiation image capturing system according to the present embodiment thus makes it possible to share the image capturing instruction information for thereby allowing the radiological technician (operator) to easily change order information supplied from the RIS by the doctor depending on the situation at the site where the patient is to be imaged, in case the process according to the order information supplied from the RIS by the doctor is inappropriate to be performed.

The radiation image capturing system also makes it possible to share a process of processing (e.g., correcting) radiation image information for thereby allowing a process of correcting radiation image information captured by an image capturing apparatus to be carried out by not only a processor associated with the image capturing apparatus, but also other processors. Therefore, a queuing time for the process of correcting the radiation image information can greatly be shortened even if image capturing apparatus and processors for controlling the image capturing apparatus are combined in a plurality of pairs.

Consequently, the radiation image capturing system 10 according to the present embodiment allows an image capturing process to be performed suitably and quickly depending on the situation at the site where the patient is to be imaged, leading to an effective reduction in a queuing time before the image capturing process starts and an image processing time subsequent to the image capturing process. It is also effective in lessening a burden to the patient etc.

In the above illustrated embodiment, the radiation image capturing system 10 has the first host console 16A for controlling a system including the first console 18A for controlling the first image capturing apparatus 20A, which is of an upstanding type incorporating the radiation detector 70 in the form of a solid-state image capturing device, and the second console 18B for controlling the second image capturing apparatus 20B compatible with the cassette 110 incorporating the stimulable phosphor panel P therein, and the second host console 16B for controlling a system including the third console 18C for controlling the third image capturing apparatus 20C, which is of an upstanding type incorporating the radiation detector 70, and the fourth console 18D for controlling the fourth image capturing apparatus 20D compatible with the cassette incorporating the stimulable phosphor panel P therein. However, the present invention is applicable to modified radiation image capturing systems as described below.

Figure 9:
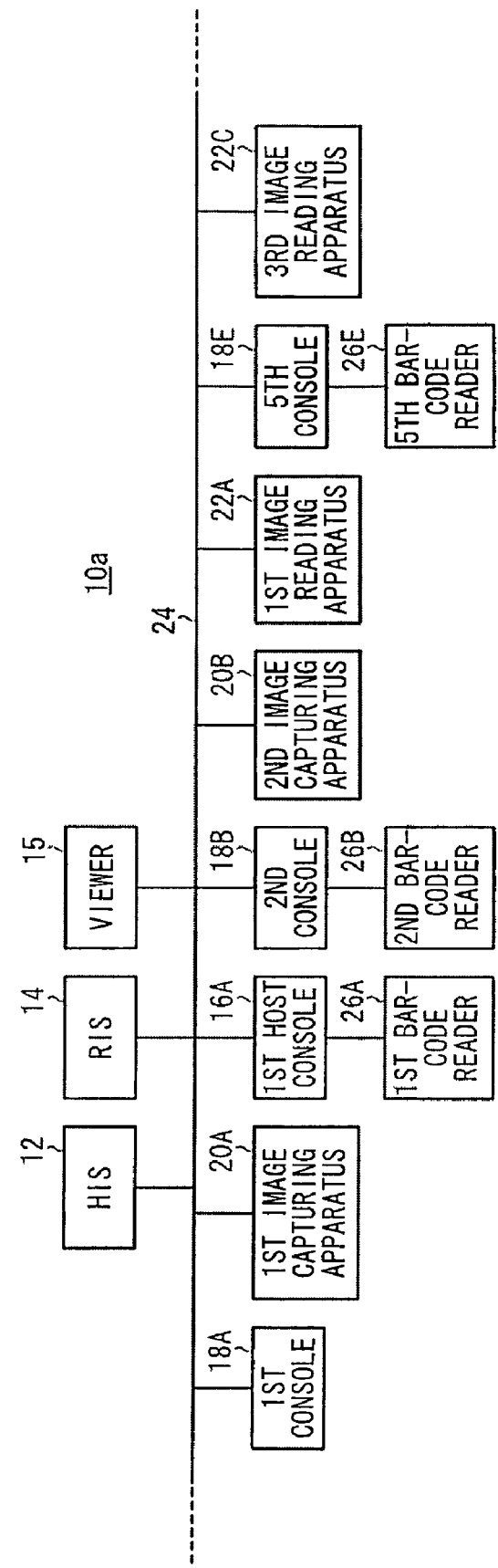
FIG. 9 is a block diagram of a radiation image capturing system according to a first modification of the present invention.

FIG. 9 shows in block form a radiation image capturing system 10a according to a first modification of the present invention. As shown in FIG. 9, the radiation image capturing system 10a includes, in addition to the first host console 16A and the related components of the radiation image capturing system 10, a fifth console 18E for controlling a fifth image capturing apparatus, not shown, compatible with a cassette incorporating a stimulable phosphor panel therein, a third reading apparatus (image reading apparatus) 22C for reading radiation image information captured by the fifth image capturing apparatus 20E, and a fifth bar-code reader 26E connected to the fifth console 18E. The present invention is applicable to the first modification.

Figure 10:
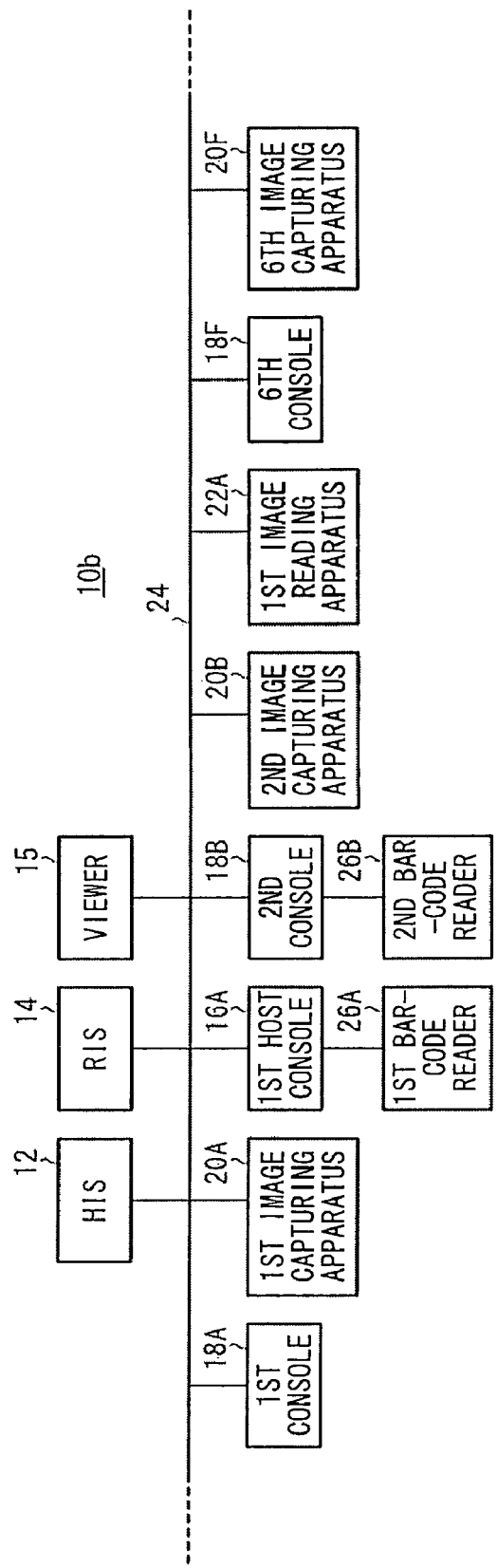
FIG. 10 is a block diagram of a radiation image capturing system according to a second modification of the present invention.

FIG. 10 shows in block form a radiation image capturing system 10b according to a second modification of the present invention. As shown in FIG. 10, the radiation image capturing system 10b includes, in addition to the first host console 16A and the related components of the radiation image capturing system 10, a sixth console 18F for controlling a sixth image capturing apparatus 20F, which may be of an upstanding type incorporating the radiation detector 70. The present invention is applicable to the second modification.

The present invention is also applicable to a radiation image capturing system including three or more host consoles or a radiation image capturing system including a combination of components described above.

The present invention is not limited to the illustrated embodiments. Rather, changes and modifications may be made to the embodiment without departing from the scope of the invention.

For example, that the second console 18B, the third console 18C, or the fourth console 18D has been selected may be displayed on the display unit of the selected console, rather than on the display unit 216 of the first host console 16A or the display unit of the second host console 16B.

In the illustrated embodiments, the radiation detector 70 which comprises the solid-state image capturing device shown in FIG. 4 is incorporated in the first image capturing apparatus 20A. However, the stimulable phosphor panel P and an image reader for reading radiation image information recorded in the stimulable phosphor panel P may be incorporated in the first image capturing apparatus 20A. In this case, after radiation image information is captured by the second image capturing apparatus 20B, it is read by the first reading apparatus 22A. At the same time, radiation image information can be captured and read by the first image capturing apparatus 20A. Accordingly, radiation image information can efficiently be acquired.

The radiation detector 70 which comprises the solid-state image capturing device may be applied to the second image capturing apparatus 20B. In this case, after radiation image information is captured by the second image capturing apparatus 20B, it is read from the radiation detector 70. At the same time, radiation image information can be captured by the first image capturing apparatus 20A. Accordingly, radiation image information can efficiently be acquired.

Although certain preferred embodiments of the present invention have been shown and described in detail, it should be understood that various changes and modifications may be made therein without departing from the scope of the appended claims.

What is claimed is:

1. A radiation image capturing system comprising:
   at least one first image capturing apparatus including a radiation detector for detecting a radiation which has passed through a subject in a radiation image capturing process, and converting the detected radiation into radiation image information;
   at least one second image capturing apparatus including a stimulable phosphor panel for detecting a radiation which has passed through a subject in a radiation image capturing process, converting the detected radiation into radiation image information, and carrying the radiation image information, the radiation image information being readable by a corresponding image reading apparatus; and
   at least one control device for controlling at least the first image capturing apparatus, the second image capturing apparatus and the image reading apparatus based on image capturing instruction information supplied from an external source;
   wherein the control device comprises:
   a change setting unit for changing settings of the image capturing instruction information depending on whether the first image capturing apparatus, the second image capturing apparatus and the image reading apparatus are usable or not; and
   a controller for controlling the first image capturing apparatus, the second image capturing apparatus and the image reading apparatus based on the changed settings of the image capturing instruction information.

2. A radiation image capturing system according to claim 1, wherein the control device further comprises:
   a determining unit for determining whether the image capturing apparatus and the image reading apparatus which have been specified, among the at least one first image capturing apparatus, the at least one second image capturing apparatus and at least one of the image reading apparatus, by the image capturing instruction information supplied from the external source are usable or not; and
   a retriever for retrieving another image capturing apparatus, among the at least one first image capturing apparatus and the at least one second image capturing apparatus, which is usable and another image reading apparatus, among the at least one image reading apparatus, which is usable, if it is determined that the specified image capturing apparatus and the specified image reading apparatus are not usable; and
   wherein the change setting unit changes the image capturing apparatus and the image reading apparatus which have been specified by the image capturing instruction information, to the image capturing apparatus and the image reading apparatus which have been retrieved by the retriever.

3. A radiation image capturing system according to claim 2, wherein if there are plural image capturing apparatus and plural image reading apparatus which have been retrieved, the change setting unit selects one image capturing apparatus and one image reading apparatus based on a preset priority level, and changes settings of the image capturing instruction information to the selected image capturing apparatus and the selected image reading apparatus.

4. A radiation image capturing system according to claim 2, wherein if there are plural image capturing apparatus and plural image reading apparatus which have been retrieved by the retriever, the change setting unit changes the image capturing apparatus and the image reading apparatus which have been specified by the image capturing instruction information, to the plural image capturing apparatus and the plural image reading apparatus which have been retrieved.

5. A radiation image capturing system according to claim 2, wherein the image capturing apparatus and the image reading apparatus are automatically changed in settings for processing radiation image information according to image specifications of the image capturing apparatus and the image reading apparatus which have been specified.

6. A radiation image capturing system comprising:
   at least one first image capturing apparatus including a radiation detector for detecting a radiation which has passed through a subject in a radiation image capturing process, and converting the detected radiation into radiation image information;
   at least one second image capturing apparatus including a stimulable phosphor panel for detecting a radiation which has passed through a subject in a radiation image capturing process, converting the detected radiation into radiation image information, and carrying the radiation image information;
   at least one image reading apparatus for reading and outputting the radiation image information carried by the stimulable phosphor panel or reading, processing, and outputting the radiation image information carried by the stimulable phosphor panel;
   at least one first processor associated with the at least one first image capturing apparatus, for controlling the associated first image capturing apparatus and at least correcting radiation image information acquired by the first image capturing apparatus;
   at least one second processor associated respectively with the second image capturing apparatus and the image reading apparatus, for controlling the associated second image capturing apparatus and the image reading apparatus, and at least correcting radiation image information acquired by the image reading apparatus; and
   at least one control device for controlling at least the first processor and the second processor based on image capturing instruction information supplied from an external source;
   wherein the control device comprises:
   a correction controller for controlling another processor or another image reading apparatus to correct the radiation image information if the radiation image information acquired by the first image capturing apparatus cannot be corrected by the associated first processor or the radiation image information acquired by the second image capturing apparatus cannot be corrected by the associated second processor or the image reading apparatus.

7. A radiation image capturing system according to claim 6, wherein the correction controller retrieves the other processor or the other image reading apparatus to correct the radiation image information, controls the one of the processors and the image reading apparatus, which cannot correct the radiation image information, to send at least the radiation image information to the other processor or the other image reading apparatus which has been retrieved, and controls the retrieved other processor or the retrieved other image reading apparatus to return the corrected radiation image information to the one of the processors and the image reading apparatus, which cannot correct the radiation image information.

* * * * *